United States Patent
Deane

(10) Patent No.: US 11,464,732 B2
(45) Date of Patent: *Oct. 11, 2022

(54) LIP SCRUB COMPOSITION

(71) Applicant: Jeffrey Alan Deane, Los Angeles, CA (US)

(72) Inventor: Jeffrey Alan Deane, Los Angeles, CA (US)

( * ) Notice: Subject to any disclaimer, the term of this patent is extended or adjusted under 35 U.S.C. 154(b) by 5 days.

This patent is subject to a terminal disclaimer.

(21) Appl. No.: 16/576,614

(22) Filed: Sep. 19, 2019

(65) Prior Publication Data

US 2020/0170925 A1    Jun. 4, 2020

Related U.S. Application Data

(60) Provisional application No. 62/774,026, filed on Nov. 30, 2018.

(51) Int. Cl.
*A61K 8/97* (2017.01)
*A61K 8/67* (2006.01)
*A61Q 19/00* (2006.01)

(52) U.S. Cl.
CPC .................. *A61K 8/97* (2013.01); *A61K 8/67* (2013.01); *A61Q 19/001* (2013.01); *A61K 2800/28* (2013.01); *A61K 2800/48* (2013.01); *A61K 2800/522* (2013.01); *A61K 2800/524* (2013.01); *A61K 2800/59* (2013.01)

(58) Field of Classification Search
None
See application file for complete search history.

(56) References Cited

U.S. PATENT DOCUMENTS 6,001,374 A * 12/1999 Nichols .................... A61K 8/73
424/401
2005/0266064 A1* 12/2005 McCarthy ............ A61K 31/401
424/450
2013/0319889 A1* 12/2013 DeSantis ................... A61J 1/00
206/438
2015/0374769 A1   12/2015 Hines et al.
2016/0030567 A1*  2/2016 Blakeslee .............. A61K 35/76
424/537
2017/0136077 A1   5/2017 Hines et al.
2018/0193250 A1   7/2018 Faller et al.

OTHER PUBLICATIONS

Mishra (10 best Way to Naturally Plumpy and Sexy Lips—Natural lip plumper; https://web.archive.org/web/20170911010008/https://indiafashionblogger.com/best-way-naturally-plumpy-sexy-lips-natural-lip-plumper/—web archived version from Nov. 9, 2017).*
Sharma ("Korres Lemon Lip Scrub;" https://web.archive.org/web/20170615005358/makeup.lovetoknow.com/Korres_Lemon_Lip_Scrub—web archived version from Jun. 2017).*
Sharma, Tanya, "Korres Lemon Lip Scrub", 2019, accessed online on Sep. 19, 2019 at: https://makeup.lovetoknow.com/Korres_Lemon_Lip_Scrub.
Premier Specialties, Inc., "Natural Cosmetic Ingredients: Functional—Natural Exfoliants and Powders", accessed online on Sep. 19, 2019 at: https://www.premierfragrances.com/natural-cosmetic-ingredients/natural-exfoliants-and-powders/.
Final Office Action of the USPTO dated Sep. 13, 2021 for related U.S. Appl. No. 16/576,607.
Non-Final Office Action of the USPTO dated Apr. 19, 2022 for related U.S. Appl. No. 16/576,607.
Non-Final Office Action of the USPTO dated Mar. 23, 2021 for related U.S. Appl. No. 16/576,607.

* cited by examiner

Primary Examiner — Susan Hoffman
(74) Attorney, Agent, or Firm — Womble Bond Dickinson (US) LLP

(57) ABSTRACT

A lip scrub composition including an emollient, a botanical, an exfoliator, the exfoliator comprising *Oryza sativa* Rice Powder and *Citrus limon* Peel Powder, and a lip plumper, the lip plumper comprising Sodium Hyaluronate, *Arnica montana* Flower Extract and Phytonadione.

16 Claims, No Drawings

LIP SCRUB COMPOSITION

CROSS-REFERENCE TO RELATED APPLICATION

The application is a non-provisional application of U.S. Provisional Patent Application No. 62/774,026, filed Nov. 30, 2018, all of which is incorporated herein by reference.

BACKGROUND

Field

Lip care compositions. More specifically, a lip care scrub, or the like.

Background

There are a wide variety of lip care products on the market. For example, one common lip care product on the market are lip balms which are contained in a lipstick-style tube and applied using the tube to the lips. Some lip balms such as ChapStick® are formulated to prevent and/or protect chafed, chapped, sunburned, cracked, and windburned lips. Often times, however, lip balms include ingredients such as phenol, menthol and/or salicylic acid, which have been found to actually dry out the user's lips.

SUMMARY

In one aspect, the invention is directed to a lip scrub composition including an emollient; a botanical; an exfoliator, the exfoliator comprising *Oryza sativa* Rice Powder and *Citrus limon* Peel Powder; and a lip plumper, the lip plumper comprising Sodium Hyaluronate, *Arnica montana* Flower Extract and Phytonadione. The exfoliator may include *Oryza sativa* Rice Powder in an amount of from 3% to less than 10% by weight of the total composition and *Citrus limon* Peel Powder in an amount of from 3% to less than 10% by weight of the total composition. The lip plumper may include Sodium Hyaluronate in an amount of from 0.01% to less than 0.1% by weight of the composition, *Arnica montana* Flower Extract in an amount of from 0.01% to less than 0.1% by weight of the composition and Phytonadione in an amount of from 0.01% to less than 0.1% by weight of the composition. In some aspects, the emollient may include a number of emollients, which in combination, are in an amount of at least 60% by weight of the total composition. The emollient may include Vegetable Oil, Paraffinum Liquidum, *Helianthus annuus* Seed Oil, *Butyrospermum parkii* Unsaponifiables, Polyglycerin-3, Mango Butter, *Cocos nucifera* (Coconut) Oil, *Theobroma grandiflorum* Seed Butter, *Schinziophyton rautanenii* Seed Oil, *Persea gratissima* Oil, *Orbignya oleifera* Seed Oil, Hydrogenated Moringa Oil Esters, *Punica granatum* Seed Oil, *Oenothera biennis* Oil and *Camellia kissi* Seed Oil. The botanical may include a number of botanicals, which in combination, are in an amount of at least 6% by weight of the total composition. For example, the botanical may include Jojoba Esters, *Vanilla planifolia* Fruit Extract, *Avena sativa* Kernel Oil, *Aloe barbadensis* Leaf Extract, *Lavandula angustifolia* Oil, and *Bambusa vulgaris* (Bamboo) Water. The lip scrub may further include a thickener; a vitamin; an antioxidant; a emulsifier; a humectant; and a film former. The thickener may include a combination of Ozokerite Wax, Beeswax, Mango Butter, and *Euphorbia cerifera* Wax. The vitamin may include a combination of Tocopheryl Acetate and Ascorbyl Palmitate. The preservative may be Hydroxyacetophenone. The emulsifier may include a combination of Glyceryl Caprylate and Cetyl Esters. The humectant may include *Crambe abyssinica* Seed Oil. The film former may include a combination of *Acacia decurrens* Flower Wax, *Helianthus annuus* Seed Wax, and *Citrus aurantium dulcis* Peel Wax.

In still further aspects, a lip scrub composition is provided including an emollient; a thickener; an exfoliator, the exfoliator comprising *Oryza sativa* Rice Powder and *Citrus limon* Peel Powder; a botanical; a vitamin; an antioxidant; a preservative; an emulsifier; a humectant; and a film former. The exfoliator may include *Oryza sativa* Rice Powder in an amount of 3% to less than 10% by weight of the total composition and *Citrus limon* Peel Powder in an amount of from 3% to less than 10% by weight of the total composition. The botanical may include *Arnica montana* Flower Extract in an amount of 0.01% to 0.09% by weight of the total composition, the vitamin comprises Phytonadione in an amount of 0.01% to 0.09% by weight of the total composition and the humectant comprises Sodium Hyaluronate in an amount of 0.01% to 0.09%, which in combination increase a volume of a users lips when applied. The botanical may include at least one botanical selected from the group consisting of *Avena sativa* (Oat) Kernel Oil, Jojoba Esters, *Aloe barbadensis* Leaf Extract and *Bambusa vulgaris* Water. The composition may include, for example, at least 60% by weight emollient; at least 6% by weight thickener; at least 6% by weight exfoliator; at least 3% by weight botanical; at least 0.1% by weight vitamin; at least 0.3% by weight antioxidant; at least 0.5% by weight preservative; at least 0.6% by weight emulsifier; at least 0.02% by weight humectant; and at least 1% by weight film former.

In still further aspects, composition is disclosed including at least 30% by weight Vegetable Oil; 10% to 30% by weight Paraffinum Liquidum; 10% to 30% by weight *Helianthus annuus* Seed Oil; 10% to 30% by weight *Butyrospermum parkii* Unsaponifiables; 3% to 10% by weight Ozokerite Wax; 3% to 10% by weight Beeswax; 3% to 10% by weight *Oryza sativa* Powder; 3% to 10% by weight *Citrus limon* Peel Powder; 3% to 10% by weight Jojoba Esters; 1% to 3% by weight *Acacia decurrens* Flower Wax; 0.3% to 1% by weight *Vanilla planifolia* Fruit Extract; 0.3% to 1% by weight Glyceryl Caprylate; 0.3% to 1% by weight *Helianthus annuus* Seed Wax; 0.3% to 1% by weight Tocopherol; 0.3% to 0.7% by weight Hydroxyacetophenone; 0.3% to 1% by weight Cetyl Esters; 0.3% to 1% by weight *Avena sativa* Kernel Oil; 0.1% to 0.3% by weight Tocopheryl Acetate; 0.1% to 0.3% by weight Polyglycerin-3; 0.1% to 0.3% by weight Mango Butter; 0.1% to 0.3% by weight *Euphorbia cerifera* Wax; 0.1% to 0.3% by weight *Copernicia cerifera* Wax; 0.1% to 0.3% by weight *Cocos nucifera* Oil; 0.1% to 0.3% by weight *Aloe barbadensis* Leaf Extract; 0.01% to 0.1% by weight *Lavandula angustifolia* Oil; 0.01% to 0.1% by weight Ascorbyl Palmitate; 0.01% to 0.1% by weight *Theobroma grandiflorum* Seed Butter; 0.01% to 0.1% by weight *Schinziophyton rautanenii* Seed Oil; 0.01% to 0.1% by weight *Persea gratissima* Oil; 0.01% to 0.1% by weight *Orbignya oleifera* Seed Oil; 0.01% to 0.1% by weight Hydrogenated Moringa Oil Esters; 0.01% to 0.1% by weight *Crambe abyssinica* Seed Oil; 0.01% to 0.1% by weight *Punica granatum* Seed Oil; 0.01% to 0.1% by weight *Oenothera biennis* Oil; 0.01% to 0.1% by weight *Camellia kissi* Seed Oil; 0.01% to 0.1% by weight *Citrus aurantium dulcis* Peel Wax; 0.01% to 0.1% by weight Sodium Hyaluronate; 0.01% to 0.1% by weight *Bambusa vulgaris* Water;

0.01% to 0.1% by weight *Arnica montana* Rower Extract; and 0.01% to 0.1% by weight Phytonadione.

The above summary does not include an exhaustive list of all aspects of the present invention. It is contemplated that the invention includes all compositions that can be practiced from all suitable combinations of the various aspects summarized above, as well as those disclosed in the Detailed Description below and particularly pointed out in the claims filed with the application. Such combinations have particular advantages not specifically recited in the above summary.

DETAILED DESCRIPTION

In one embodiment, the lip care composition disclosed herein is a restorative lip care composition formulated to restore, moisturize and/or treat dry, parched lips and lock in long-lasting moisture. In some embodiments, the composition is a topical product, for example, a topical lip care product such as a lip stick, a lip balm, a lip scrub, or the like. Although representative compositions forms are disclosed, it should be understood that the composition may be in any form suitable for application to a user's lips.

The composition may include several key ingredients in amounts, which in combination, work synergistically, to care for a user's lips. For example, the key ingredients may have a restorative, a moisturizing, a lip plumping, a scrubbing, and/or an exfoliating effect, to name a few. The combination of ingredients are specifically selected and combined to form a composition, for example a lip care or treatment composition.

Lip Stick

Representatively, in one embodiment, the composition may by a lip treatment stick or balm including a synergistic combination of one or more of an emollient(s), thickener(s), botanical(s), antioxidant(s), plumping agent(s) emulsifiers(s), vitamin(s), humectant(s), film former(s), calming agent(s) and/or sweeteners(s). Additionally, the composition may include a colorant(s).

In one embodiment, the composition balances one or more emollient(s), thickeners(s), botanical(s), antioxidants(s), plumping agent(s) emulsifiers(s), vitamin(s), humectant(s), film formers(s), calming agent(s), sweeteners(s) and/or colorant(s) in amounts sufficient to provide a composition that effectively nourishes, moisturizes, restores, treats and/or plumps the lips when it is applied.

Representatively, in one aspect, the lip care composition may include, among others, ingredients and/or agents such as Paraffin, Shea butter, Beeswax, essential oils, Vitamin C & E and/or Bamboo Water, which help to moisturize, treat, restore, nourish or otherwise improve the condition of the user's lips.

Additionally, the composition may include ingredients such as Sodium Hyaluronate, *Arnica montana* Flower Extract and/or Vitamin K, which are synergistically combined to provide a lip plumping effect when applied topically to the lips. The phrase "lip plumping" is intended to refer to any increase in lip volume, and for any period of time (e.g., hours). Thus, a lip plumping agent may be any agent or ingredient that has the effect of increasing lip volume when topically applied to the lips.

Representatively, it is believed that when topically applied, Sodium Hyaluronate can facilitate the absorption or penetration of other agents, such as moisturizing agents or other agents that may have a lip plumping effect, through the skin. Thus, when combined synergistically with other agents, for example a moisturizing agent(s) or other lip plumping agents, the enhanced absorption causes an increase in lip volume for a period of time. For example, Sodium Hyaluronate may be synergistically combined with *Arnica montana* Flower Extract and/or Vitamin K to achieve maximum lip plumping.

In some aspects, the lip care composition may be a translucent lip care composition in that it does not have any added color or tint. In other aspects, the lip care composition may be a tinted lip care composition which includes an additive which adds tint or color to the lips once the composition is applied. In addition, it should be recognized that while the composition is described in some embodiments as a lip stick, the lip care composition may be in any form suitable for application to the user's lips and a container of any shape/size, and is not limited to the shape of a stick, or baton. For example, the lip care composition may be a lip balm, lip stick, lip cream, lip gel, lip gloss, or the like, that can be used in any size/shape container. The composition may be applied to the lips directly, or rubbed on the user's finger and then applied to the lips.

Representatively, in one aspect, a balanced lip care composition includes from about 60 percent (%) to about 100% by weight emollient(s), from about 6% to 21% by weight thickening agent(s), from about 0.5% to 2% by weight botanical agent(s), from about 0.3% to 1% by weight antioxidant(s), from about 0.3% to 1% by weight emulsifier(s), from about 0.1% to 0.5% by weight vitamin(s), from about 0.02% to 0.2% by weight humectant(s), from about 0.01-0.1% by weight film forming agent(s), from about 0.01% to 0.1% by weight calming agent(s), and/or from about 0.01% to 0.1% by weight sweetener(s). In addition, a combination of one or more of plumping agent(s) may be included in the composition in an amount of about 0.01% to 0.27% to effectively provide a lip plumping effect. In other embodiments, the composition can contain any one or more of the agents or ingredients disclosed herein, in any amounts and any combinations sufficient to nourish, moisturize, restore, treat and/or plumps the lips when it is applied.

Representatively, in another aspect, a balanced lip care composition including a tint includes from about 50 percent (%) to about 100% by weight emollient(s), from about 5% to 25% by weight thickening agent(s), from about 0.6% to 2.5% by weight botanical agent(s), from about 0.1% to 0.3% by weight antioxidant(s), from about 0.3% to 1% by weight emulsifier(s), from about 0.1% to 0.6% by weight vitamin(s), from about 0.02% to 0.2% by weight humectant(s), from about 0.02%-0.2% by weight film forming agent(s), from about 0.01% to 0.1% by weight calming agent(s), from about 0.01% to 0.1% by weight sweetener(s), and/or from about 0.09% to 0.9% colorant(s), in amounts sufficient to provide a composition that effectively moisturize, treat, restore, nourish or otherwise improve the condition of the user's lips. In addition, a combination of one or more of plumping agent(s) may be included in the composition in an amount of about 0.01% to 0.27% to effectively provide a lip plumping effect. In other embodiments, the composition can contain any one or more of the agents or ingredients disclosed herein, in any amounts and any combinations sufficient to nourish, moisturize, restore, treat and/or plumps the lips when it is applied.

A representative emollient(s) may include, but is not limited to, vegetable oil (virgin olive oil based), paraffinum liquidum, *Helianthus annuus* (Sunflower) Seed Oil, *Butyrosperum parkii* (Shea Butter) Unsaponafiables, Nylon-11, *Butyrosperum parkii* (Shea Butter) Extract, Mango (*Mangifera indica*) Butter, *Cocos nucifera* (Coconut) Oil, *Mela-*

*leuca alternifolia* (Tea Tree) Leaf Oil, *Theobroma grandiflorum* (Cupuacu) Seed Butter, *Schinzeiophyton rautanenii* (Mongongo) Seed Oil, *Persa gratissima* (Avocado) Oil, *Obignya oleifera* Seed (Babassu Nut) Oil, Hydrogenated Moringa Oil Esters, *Punica granatum* (Pomegranate) Seed Oil, *Oenothera biennis* (Evening Primrose) Oil, *Camellia kissi* (Sasanqua) Seed Oil, *Ricinus communis* (castor) seed oil, hydrogenated vegetable oil, and/or squalene.

A representative thickening agent(s) may include, but is not limited to, Ozokerite Wax, Beeswax, Nylon-11, *Euphorbia cerifera* (Candelilla) Wax, and/or *Copernicia cerifera* (Carnauba) Wax.

The term "botanical agent" as used herein refers to plant derived products such as plant extracts and essential oils derived from plants. A representative botanical agent(s) may include, but is not limited to, *Vanilla planifolia* Fruit Extract, *Avena sativa* (Oat) Kernel Oil, *Lavandula angustifolia* (Lavender) Oil, *Aloe barbadensis* (*Aloe vera*) Leaf Extract, *Bambusa vulgaris* (Bamboo) Water, and/or *Arnica montana* Flower Extract.

A representative antioxidant(s) may include, but is not limited to, tocopherol.

A representative emulsifier(s) may include, but is not limited to, cetyl esters.

A representative vitamin(s) may include, but is not limited to, Tocopheryl Acetate (Vitamin E Acetate), Beta-Sitosterol, Ascorbyl Palmitate (Vitamin C Palmitate) and/or Phytonadione (Vitamin K1).

A representative humectant(s) may include, but is not limited to, Glycerin, *Crambe abyssinica* (Abyssinian) Seed Oil and Sodium PCA. Glycerin may be a plant derived Glycerin which has natural moisturizing factors beneficial to pets. *Crambe abyssinica* (Abyssinian) Seed Oil is a natural seed oil with an ultra-light, non-greasy feel which absorbs quickly and provides superior moisturizing benefits to pets.

A representative film forming agent(s) may include, but is not limited to, *Citrus aurantium dulcis* (Orange) Peel Wax and/or Triethoxycaprylylsilane.

A representative calming agent(s) may include, but is not limited to, allantoin.

A representative sweetener(s), may include, but is not limited to, sucralose.

A representative colorant(s) may include, but is not limited to, Iron Oxide (Yellow) (CI #77492), Mica, Titanium Dioxide (CAS 13663-67-7), Red 33 (CI #17200), Iron Oxide (mineral origin) (CI #77491), Red 7 (CI #15850, CAS 5281-04-9), Red 6 (CI #15850, CAS 17582-98-1), Titanium Dioxide (CI #77891, CAS 13463-67-70), and/or Black Iron Oxide (CI #77499).

A representative lip plumping agent(s) may include, but is not limited to, sodium hyaluronate, *Arnica montana* flower extract and/or Phytonadione (Vitamin K1). Representatively, in one embodiment, sodium hyaluronate may be in an amount of from about 0.01% to less than 0.1% by weight, for example, 0.01% to 0.09% by weight; *Arnica montana* Flower Extract may be in an amount of from about 0.01% to less than 0.1% by weight, for example, 0.01% to 0.09% by weight, and Phytonadione (Vitamin K1) may be in an amount of from about 0.01% to less than 0.1% by weight, for example, from 0.01% to 0.09% by weight, of the composition.

For example, in one embodiment, a lip care composition, for example, a lip stick or lip balm may be formed by combining or mixing two or more of the following ingredients or agents in the amounts (listed as percentage by weight of the total composition) as follows: at least 30% by weight Vegetable Oil (Virgin Olive Oil Based), 10% to 30% by weight Paraffinum Liquidum, 10% to 30% by weight *Helianthus annuus* (Sunflower) Seed Oil, 1% to 3% by weight *Ricinus communis* (Castor) Seed Oil, 10% to 30% by weight *Butyrospermum parkii* (Shea) Butter Extract Unsaponifiable, 0.1% to 0.3% by weight Mango (*Mangifera indica*) Butter, 0.1% to 0.3% by weight Jojoba Esters, 0.1% to 0.3% by weight Hydrogenated Vegetable Oil, 0.01% to 0.1% by weight Squalene, 0.01% to 0.1% by weight *Theobroma grandiflorum* (Cupuacu) Seed Butter, 0.01% to 0.1% by weight *Schinziophyton rautanenii* (Mongongo) Seed Oil, 0.01% to 0.1% by weight *Persea gratissima* (Avocado) Oil, 0.01% to 0.1% by weight *Orbignya oleifera* Seed (Babassu Nut) Oil, 0.01% to 0.1% by weight Hydrogenated Moringa Oil Esters, 0.01% to 0.1% by weight *Punica granatum* (Pomegranate) Seed Oil, 0.01% to 0.1% by weight *Oenothera biennis* (Evening Primrose) Oil, 0.01% to 0.1% by weight *Camellia kissi* (Sasanqua) Seed Oil, 3% to 10% by weight Ozokerite Wax, 3% to 10% by weight Beeswax, 1% to 3% by weight Nylon-11, 0.01% to 0.3% by weight *Euphorbia cerifera* (Candelilla) Wax, 0.01% to 0.3% by weight *Copernicia cerifera* (Carnauba) Wax, 0.3% to 1% by weight Tocopherol, 0.3% to 1% by weight Cetyl Esters, 0.3% to 1% *Vanilla planifolia* Fruit Extract; 0.3% to 1% by weight *Avena sativa* (Oat) Kernel Oil, 0.01% to 0.1% by weight *Lavandula angustifolia* (Lavender) Oil, 0.01% to 0.1% by weight *Aloe barbadensis* (*Aloe vera*) Leaf Extract, 0.01% to 0.1% by weight *Bambusa vulgaris* (Bamboo) Water, 0.01% to 0.1% by weight *Arnica montana* Flower Extract, 0.01% to 0.3% by weight Tocopheryl Acetate (Vitamin E Acetate), 0.01% to 0.1% by weight Beta-Sitosterol, 0.01% to 0.1% by weight Ascorbyl Palmitate (Vitamin C Palmitate), 0.01% to 0.1% by weight Phytonadione (Vitamin K1), 0.01% to 0.1% by weight *Crambe abyssinica* (Abyssinian) Seed Oil, 0.01% to 0.1% by weight Sodium Hyaluronate, 0.01% to 0.1% by weight *Citrus aurantium dulcis* (Orange) Peel Wax, 0.01% to 0.1% by weight Triethoxycaprylylsilane, 0.01% to 0.1% by weight Allantoin, 0.01% to 0.1% by weight Sucralose, 0.01% to 0.1% by weight Iron Oxide (CI #77492), 0.01% to 0.1% by weight Mica, 0.01% to 0.1% by weight Titanium Dioxide, 0.01% to 0.1% by weight Red 33 (CI #17200), 0.01% to 0.1% by weight Iron Oxide (CI #77491), 0.01% to 0.1% by weight C115850, 0.01% to 0.1% by weight Red 6 (CI #15850), 0.01% to 0.1% by weight CI 77891 (Titanium Dioxide), and/or 0.01% to 0.1% by weight CI 77499.

Lip Scrub

In other embodiments, the composition may by a lip scrub. The composition may be considered a lip scrub in that it includes an abrasive, or other exfoliating agent, specifically designed to remove dead skin cells from the lips. Exfoliation of the lips is believed to enhance absorption of agents (e.g., moisturizing agents) because it removes dead skin cells which can prevent absorption, or otherwise act as a barrier, to treatment or lip care agents (e.g., moisturizing agents).

The lip scrub may include a synergistic combination of one or more of an abrasive(s), emollient(s), thickeners(s), botanical(s), antioxidant(s), plumping agent(s), emulsifier(s), vitamin(s), humectant(s), film former(s) and/or preservative(s).

In one embodiment, the composition balances one or more emollient(s), thickener(s), abrasive(s), botanical(s), antioxidant(s), plumping agent(s), emulsifiers(s), vitamin(s), humectant(s), film formers(s) and/or preservative(s) in amounts sufficient to provide a composition that effectively nourishes, moisturizes, restores, treats, plumps, scrubs and/or exfoliates the lips when it is applied.

Representatively, in one aspect, the lip care composition may be a lip scrub which includes, among other ingredients, an exfoliant or abrasive designed to gently exfoliate the lips by buffing away dead, dry skin cells. The exfoliating or abrasive agent may be an agent other than sugar, and which is gentler than sugar at exfoliating the lips. In one aspect, the exfoliating or abrasive agent may be *Citrus limon* (Lemon) Peel Powder. *Citrus limon* (Lemon) Peel Powder may consist of granules of powder obtained from the peel of a lemon. The granules are incorporated into the lip scrub such that when the lip scrub is applied or rubbed onto the lips, it acts as a gentle abrasive that can remove dead skin cells from the lips.

In addition, the lip scrub may further include, among others, ingredients such as paraffin, rhea butter, beeswax, essential oils, vitamin C & E and/or bamboo water, which help to exfoliate, moisturize, treat, restore, nourish or otherwise improve the condition of the user's lips. Additionally, the composition may include ingredients such as sodium hyaluronate, *Arnica montana* flower extract and/or Vitamin K, which are synergistically combined to provide a lip plumping effect when applied to the lips. In addition, it should be recognized that the composition may be in any form suitable for application to the user's lips, and is not limited to any particular form and/or shaped container. For example, the lip scrub may be a lip balm, lip stick, lip cream, lip gel, lip gloss, or the like, that can be used in any size/shape container. The composition may be applied to the lips directly, or rubbed on the user's finger and then applied to the lips.

Representatively, in one aspect, a balanced lip scrub composition includes from about 60 percent (%) to about 100% by weight emollient(s), from about 6% to 21% by weight thickening agent(s), from about 3% to 13% by weight botanical agent(s), from about 3% to 10% abrasive, from about 0.3% to 1% by weight antioxidant(s), from about 0.5% to 2% by weight emulsifier(s), from about 2.5% to 6% a preservative, from about 0.1% to 0.5% by weight vitamin(s), from about 0.02% to 0.2% by weight humectant(s), and/or from about 1.3% to 4.1% by weight film forming agent(s). In addition, a combination of one or more of plumping agent(s) may be included in the composition in an amount of about 0.01% to 0.27% to effectively provide a lip plumping effect. In other embodiments, the composition can contain any one or more of the agents or ingredients disclosed herein, in any amounts and any combinations sufficient to exfoliate, nourish, moisturize, restore, treat and/or plumps the lips when it is applied.

A representative emollients) may include, but is not limited to, vegetable oil (virgin olive oil based), paraffinum liquidum, *Helianthus annuus* (Sunflower) Seed Oil, *Butyrosperum parkii* (Shea Butter) Unsaponafiables, polyglycerin-3, Mango (*Mangifera indica*) Butter, *Cocos nucifera* (Coconut) Oil, *Theobroma grandiflorum* (Cupuacu) Seed Butter, *Schinzeiophyton rautanenii* (Mongongo) Seed Oil, *Persa gratissima* (Avocado) Oil, *Obignya oleifera* Seed (Babassu Nut) Oil, Hydrogenated Moringa Oil Esters, *Punica granatum* (Pomegranate) Seed Oil, *Oenothera biennis* (Evening Primrose) Oil, and/or *Camellia kissi* (Sasanqua) Seed Oil.

A representative thickening agent(s) may include, but is not limited to, Ozokerite Wax, Beeswax, Mango (*Mangifera indica*) Butter, and/or *Euphorbia cerifera* (Candelilla) Wax.

A representative botanical agent(s) may include, but is not limited to, *Oryza sativa* (Rice) Powder, Jojoba Esters, *Vanilla planifolia* Fruit Extract, *Avena sativa* (Oat) Kernel Oil, *Lavandula angustifolia* (Lavender) Oil, *Aloe barbadensis* (*Aloe Vera*) Leaf Extract, *Bambusa vulgaris* (Bamboo) Water, and/or *Arnica montana* Flower Extract.

A representative abrasive(s) may include, but is not limited to, *Citrus limon* Peel Powder and/or *Oryza sativa* (Rice) Powder. The abrasive(s) may be combined in critical amounts which have been found to maximize exfoliation of the lips. Representatively, in one embodiment, *Citrus limon* Peel Powder may be in an amount of from about 2.5% to 10% by weight, for example, 3% to 9.99% by weight, and/or *Oryza sativa* (Rice) Powder may be in an amount of from about 2.5% to 10% by weight, for example, 3% to 9.99% by weight, of the composition.

A representative antioxidant(s) may include, but is not limited it, tocopherol.

A representative emulsifier(s) may include, but is not limited to, cetyl esters and/or glyceryl caprylate.

A representative preservative(s) may include, but is not limited to, Hydroxyacetophenone (i.e., Ethanone).

A representative vitamin(s) may include, but is not limited to, Tocopheryl Acetate (Vitamin E Acetate), Ascorbyl Palmitate (Vitamin C Palmitate) and/or Phytonadione (Vitamin K1).

A representative humectant(s) may include, but is not limited to, *Crambe abyssinica* (Abyssinian) Seed Oil and/or Sodium Hyaluronate.

A representative film forming agent(s) may include, but is not limited to, *Acacia decurrens* (*mimosa*) Flower Wax, *Helianthus annuus* (Sunflower) Seed Wax and/or *Citrus aurantium dulcis* (Orange) Peel Wax.

A representative plumping agent(s) may include, but is not limited to, as sodium hyaluronate, *ARNICA montana* flower extract and/or Phytonadione (Vitamin K1). The plumping agents may be combined in critical amounts which have been found to maximize the lip plumping effect. Representatively, in one embodiment, sodium hyaluronate may be in an amount of from about 0.01% to less than 0.1% by weight, for example, 0.01% to 0.09% by weight, *Arnica montana* Flower Extract may be in an amount of from about 0.01% to less than 0.1% by weight, for example, 0.01% to 0.09% by weight, and Phytonadione (Vitamin K1) may be in an amount of from about 0.01% to less than 0.1% by weight, for example, from 0.01% to 0.09% by weight, of the composition.

For example, in one embodiment, the lip scrub may be formed by combining or mixing two or more ingredients or agents in the amounts (listed as percentage by weight of the total composition) as follows: at least 30% by weight Vegetable Oil (Virgin Olive Oil Based), 10% to 30% Paraffinum Liquidum, 10% to 30% by weight *Helianthus annuus* (Sunflower) Seed Oil, 10% to 30% by weight *Butyrospermum parkii* (Shea Butter) Unsaponifiables, 0.1% to 0.3% by weight Polyglycerin-3, 0.1% to 0.3% by weight Mango (*Mangifera indica*) Butter, 0.1% to 0.3% by weight *Cocos nucifera* (Coconut) Oil, 0.01% to 0.1% by weight *Theobroma grandiflorum* (Cupuacu) Seed Butter, 0.01% to 0.1% by weight *Schinziophyton rautanenii* (Mongongo) Seed Oil, 0.01% to 0.1% by weight *Persea gratissima* (Avocado) Oil, 0.01% to 0.1% by weight *Orbignya oleifera* Seed (Babassu Nut) Oil, 0.01% to 0.1% by weight Hydrogenated Moringa Oil Esters, 0.01% to 0.1% by weight *Punica granatum* (Pomegranate) Seed Oil, 0.01% to 0.1% by weight *Oenothera biennis* (Evening Primrose) Oil, 0.01% to 0.1% by weight *Camellia kissi* (Sasanqua) Seed Oil, 3% to 10% by weight Ozokerite Wax, 3% to 10% by weight Beeswax, 0.1% to 0.3% by weight Mango (*Mangifera indica*) Butter, 0.1% to 0.3% by weight *Euphorbia cerifera*

(Candelilla) Wax, 3% to 10% by weight *Citrus limon* Peel Powder, 0.3% to 1% by weight Tocopherol, 0.3% to 1% by weight Glyceryl Caprylate, 0.3% to 1% by weight Cetyl Esters, 0.3% to 0.7% by weight Hydroxyacetophenone (aka Ethanone), 3% to 10% by weight *Oryza sativa* (Rice) Powder, 3% to 10% by weight Jojoba Esters, 0.3% to 1% by weight *Vanilla planifolia* Fruit Extract, 0.3% to 1% by weight *Avena sativa* (Oat) Kernel Oil, 0.1% to 0.3% by weight *Aloe barbadensis* (*Aloe vera*) Leaf Extract, 0.01% to 0.1% by weight *Lavandula angustifolia* (Lavender) Oil, 0.01% to 0.1% by weight *Bambusa vulgaris* (Bamboo) Water, 0.01% to 0.1% by weight *Arnica montana* Flower Extract, 0.1% to 0.3% by weight Tocopheryl Acetate (Vitamin E Acetate), 0.01% to 0.1% by weight Ascorbyl Palmitate (Vitamin C Palmitate), 0.01% to 0.1% by weight Phytonadione (Vitamin K1), 0.01% to 0.1% by weight *Crambe abyssinica* (Abyssinian) Seed Oil, 0.01% to 0.1% by weight Sodium Hyaluronate, 1% to 3% by weight *Acacia decurrens* (*Mimosa*) Rower Wax, 0.3% to 1% by weight *Helianthus annuus* (Sunflower) Seed Wax, and/or 0.01% to 0.1% by weight *Citrus aurantium dulcis* (Orange) Peel Wax.

Other ingredients or agents included in the composition that may not be specifically discussed above are included and described in reference to the exemplary formulations set forth below. In addition, it should further be understood that although the agents described herein are categorized according to a single function, many have multiple functions and therefore may be understood to be included under other functional categories than those listed herein.

The following specific examples set forth exemplary compositions that may be topically applied to a subject (e.g. the lips of a user). The ingredient amounts disclosed in the following examples are in effective amounts suitable for moisturizing, treating, restoring, nourishing, scrubbing, plumping or otherwise improving the condition of the area to which the composition is applied. The composition may have one of the following exemplary formulations:

Example 1

| Percent | Ingredient (INCI Name) | Function |
| --- | --- | --- |
| 30.00-100.00 | Vegetable Oil (Virgin Olive Oil Based) | Emollient |
| 10.00-29.99 | Paraffinum Liquidum | Emollient |
| 10.00-29.99 | *Helianthus Annuus* (Sunflower) Seed Oil | Emollient |
| 10.00-29.99 | *Butyrospermum Parkii* (Shea Butter) Unsaponifiables | Emollient |
| 3.00-9.99 | Ozokerite Wax | Thickener |
| 3.00-9.99 | Beeswax | Thickener |
| 1.00-2.99 | Nylon-11 | Emollient |
| 0.30-0.99 | Tocopherol | Antioxidant |
| 0.30-0.99 | Cetyl Esters | Emulsifier |
| 0.30-0.99 | *Butyrospermum Parkii* (Shea Butter) Extract | Emollient |
| 0.30-0.99 | *Avena Sativa* (Oat) Kernal Oil | Botanical |
| 0.10-0.29 | Tocopheryl Acetate (Vitamin E Acetate) | Vitamin |
| 0.10-0.29 | Mango (*Mangifera Indica*) Butter | Emollient |
| 0.10-0.29 | Jojoba Esters | Botanical |
| 0.10-0.29 | *Euphorbia Cerifera* (Candelilla) Wax | Thickener |
| 0.10-0.29 | *Copernicia Cerifera* (Carnauba) Wax | Thickener |
| 0.10-0.29 | *Cocos Nucifera* (Coconut) Oil | Emollient |
| 0.10-0.29 | *Aloe Barbadensis* (Aloe Vera) Leaf Extract | Botanical |
| 0.01-0.09 | *Melaleuca Alternifolia* (Tea Tree) Leaf Oil | Emollient |
| 0.01-0.09 | Ascorbyl Palmitate (Vitamin C Palmitate) | Vitamin |
| 0.01-0.09 | *Theobroma Grandiflorum* (Cupuacu) Seed Butter | Emollient |
| 0.01-0.09 | *Schinziophyton Rautanenil* (Mongongo) Seed Oil | Emollient |
| 0.01-0.09 | *Persea Gratissima* (Avocado) Oil | Emollient |
| 0.01-0.09 | *Orbignya Oleifera* Seed (Babasu Nut) Oil | Emollient |
| 0.01-0.09 | Hydrogenated *Moringa* Oil Esters | Emollient |
| 0.01-0.09 | *Crambe Abyssinica* (Abyssinian) Seed Oil | Humectant |
| 0.01-0.09 | *Punica Granatum* (Pomegranate) Seed Oil | Emollient |
| 0.01-0.09 | *Oenothera Biennis* (Evening Primrose) Oil | Emollient |
| 0.01-0.09 | *Camellia Kissi* (Sasanqua) Seed Oil | Emollient |
| 0.01-0.09 | *Citrus Aurantium Dulcis* (Orange) Peel Wax | Film Former |
| 0.01-0.09 | Allantoin | Calming Agent |
| 0.01-0.09 | Sucralose | Sweetener |
| 0.01-0.09 | Sodium Hyaluronate | Humectant/Plumping |
| 0.01-0.09 | *Bambusa Vulgaris* (Bamboo) Water | Botanical |
| 0.01-0.09 | *Arnica Montana* Flower Extract | Botanical/Plumping |
| 0.01-0.09 | Phytonadione (Vitamin K1) | Vitamin/Plumping |

Example 2

| Percent | Ingredient (INCI Name) | Function |
| --- | --- | --- |
| 30.00-100.00 | Vegetable Oil (Virgin Olive Oil Based) | Emollient |
| 10.00-29.99 | Paraffinum Liquidum | Emollient |
| 10.00-29.99 | *Helianthus Annuus* (Sunflower) Seed Oil | Emollient |
| 10.00-29.99 | *Butyrospermum Parkii* (Shea) Butter Unsaponifiable | Emollient |
| 3.00-9.99 | Ozokerite Wax | Thickener |
| 3.00-9.99 | Beeswax | Thickener |
| 1.00-2.99 | Nylon-11 | Thickener |
| 1.00-2.99 | *Ricinus Communis* (Castor) Seed Oil | Emollient |
| 0.30-0.99 | *Vanilla Planifolia* Fruit Extract | Botanical |

-continued

| Percent | Ingredient (INCI Name) | Function |
| --- | --- | --- |
| 0.30-0.99 | Cetyl Esters | Emulsifier |
| 0.30-0.99 | *Butyrospermum Parkii* (Shea) Butter Extract | Emollient |
| 0.30-0.99 | *Avena Sativa* (Oat) Kernal Oil | Botanical |
| 0.10-0.29 | Tocopheryl Acetate (Vitamin E Acetate) | Vitamin |
| 0.10-0.29 | Mango (*Mangifera Indica*) Butter | Emollient |
| 0.10-0.29 | Jojoba Esters | Emollient |
| 0.10-0.29 | *Euphorbia Cerifera* (Candelilla) Wax | Thickener |
| 0.10-0.29 | *Copernicia Cerifera* (Carnauba) Wax | Thickener |
| 0.10-0.29 | Hydrogenated Vegetable Oil | Emollient |
| 0.10-0.29 | Tocopherol | Antioxidant |
| 0.01-0.09 | Iron Oxide (CI#77492) | Colorant |
| 0.01-0.09 | Beta-Sitosterol | Vitamin |
| 0.01-0.09 | Mica | Colorant |
| 0.01-0.09 | Titanium Dioxide (CAS13663-67-7) | Colorant |
| 0.01-0.09 | *Lavandula Angustifolia* (Lavender) Oil | Botanical |
| 0.01-0.09 | Red 33 (CI#17200) | Colorant |
| 0.01-0.09 | Squalene | Emollient |
| 0.01-0.09 | *Aloe Barbadensis* (Aloe Vera) Leaf Extract | Botanical |
| 0.01-0.09 | Iron Oxide (CI#77491) | Colorant |
| 0.01-0.09 | Ascorbyl Palmitate (Vitamin C Palmitate) | Vitamin |
| 0.01-0.09 | Sucralose | Sweetener |
| 0.01-0.09 | *Theobroma Grandiflorum* (Cupuacu) Seed Butter | Emollient |
| 0.01-0.09 | *Schinziophyton Rautanenil* (Mongongo) Seed Oil | Emollient |
| 0.01-0.09 | *Persea Gratissima* (Avocado) Oil | Emollient |
| 0.01-0.09 | *Orbignya Oleifera* Seed (Babasu Nut) Oil | Emollient |
| 0.01-0.09 | Hydrogenated *Moringa* Oil Esters | Emollient |
| 0.01-0.09 | *Crambe Abyssinica* (Abyssinian) Seed Oil | Humectant |
| 0.01-0.09 | *Punica Granatum* (Pomegranate) Seed Oil | Emollient |
| 0.01-0.09 | *Oenothera Biennis* (Evening Primrose) Oil | Emollient |
| 0.01-0.09 | *Camellia Kissi* (Sasanqua) Seed Oil | Emollient |
| 0.01-0.09 | *Citrus Aurantium Dulcis* (Orange) Peel Wax | Film Former |
| 0.01-0.09 | Allantoin | Calming Agent |
| 0.01-0.09 | Red 7 | Colorant |
| 0.01-0.09 | Red 6 | Colorant |
| 0.01-0.09 | Titanium Dioxide (CI #77891) (CAS 13463-67-70) | Colorant |
| 0.01-0.09 | Triethoxycaprylylsilane | Film Former |
| 0.01-0.09 | Sodium Hyaluronate | Humectant/Plumping |
| 0.01-0.09 | *Bambusa Vulgaris* (Bamboo) Water | Botanical |
| 0.01-0.09 | *Arnica Montana* Flower Extract | Botanical/Plumping |
| 0.01-0.09 | Phytonadione (Vitamin K1) | Vitamin/Plumping |
| 0.01-0.09 | Black Iron Oxide (CI #77499) | Colorant |

Example 3

| Percent | Ingredient (INCI Name) | Function |
| --- | --- | --- |
| 30.00-100.00 | Vegetable Oil (Virgin Olive Oil Based) | Emollient |
| 10.00-29.99 | Paraffinum Liquidum | Emollient |
| 10.00-29.99 | *Helianthus Annuus* (Sunflower) Seed Oil | Emollient |
| 10.00-29.99 | *Butyrospermum Parkii* (Shea Butter) Unsaponifiables | Emollient |
| 3.00-9.99 | Ozokerite Wax | Thickener |
| 3.00-9.99 | Beeswax | Thickener |
| 3.00-9.99 | *Oryza Sativa* (Rice) Powder | Abrasive |
| 3.00-9.99 | *Citrus Limon* Peel Powder | Abrasive |
| 3.00-9.99 | Jojoba Esters | Botanical |
| 1.00-2.99 | *Acacia Decurrens* (Mimosa) Flower Wax | Film Former |
| 0.30-0.99 | *Vanilla Planifolia* Fruit Extract | Botanical |
| 0.30-0.99 | Glyceryl Caprylate | Emulsifier |
| 0.30-0.99 | *Helianthus Annuus* (Sunflower) Seed Wax | Film Former |
| 0.30-0.99 | Tocopherol | Antioxidant |
| 0.5 | Hydroxyacetophenone (aka Ethanone) | Preservative |
| 0.30-0.99 | Cetyl Esters | Emulsifier |
| 0.30-0.99 | *Avena Sativa* (Oat) Kernal Oil | Botanical |
| 0.10-0.29 | Tocopheryl Acetate (Vitamin E Acetate) | Vitamin |
| 0.10-0.29 | Polyglycerin-3 | Emollient |
| 0.10-0.29 | Mango (*Mangifera Indica*) Butter | Emollient |
| 0.10-0.29 | *Euphorbia Cerifera* (Candelilla) Wax | Thickener |
| 0.10-0.29 | *Copernicia Cerifera* (Carnauba) Wax | Thickener |
| 0.10-0.29 | *Cocos Nucifera* (Coconut) Oil | Emollient |
| 0.10-0.29 | *Aloe Barbadensis* (Aloe Vera) Leaf Extract | Botanical |
| 0.01-0.09 | *Lavandula Angustifolia* (Lavender) Oil | Botanical |
| 0.01-0.09 | Ascorbyl Palmitate (Vitamin C Palmitate) | Vitamin |
| 0.01-0.09 | *Theobroma Grandiflorum* (Cupuacu) Seed Butter | Emollient |
| 0.01-0.09 | *Schinziophyton Rautanenil* (Mongongo) Seed Oil | Emollient |

-continued

| Percent | Ingredient (INCI Name) | Function |
| --- | --- | --- |
| 0.01-0.09 | *Persea Gratissima* (Avocado) Oil | Emollient |
| 0.01-0.09 | *Orbignya Oleifera* Seed (Babasu Nut) Oil | Emollient |
| 0.01-0.09 | Hydrogenated *Moringa* Oil Esters | Emollient |
| 0.01-0.09 | *Crambe Abyssinica* (Abyssinian) Seed Oil | Humectant |
| 0.01-0.09 | *Punica Granatum* (Pomegranate) Seed Oil | Emollient |
| 0.01-0.09 | *Oenothera Biennis* (Evening Primrose) Oil | Emollient |
| 0.01-0.09 | *Camellia Kissi* (Sasanqua) Seed Oil | Emollient |
| 0.01-0.09 | *Citrus Aurantium Dulcis* (Orange) Peel Wax | Film Former |
| 0.01-0.09 | Sodium Hyaluronate | Humectant/Plumping |
| 0.01-0.09 | *Bambusa Vulgaris* (Bamboo) Water | Botanical |
| 0.01-0.09 | *Arnica Montana* Flower Extract | Botanical/Plumping |
| 0.01-0.09 | Phytonadione (Vitamin K1) | Vitamin/Plumping |

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

In the foregoing specification, the invention has been described with reference to specific embodiments thereof. It will, however, be evident that various modifications and changes can be made thereto without departing from the broader spirit and scope of the invention as set forth in the appended claims. The specification and drawing are, accordingly, to be regarded in an illustrative rather than a restrictive sense.

The invention claimed is:

1. A lip scrub composition comprising:
   an emollient comprising a combination of emollients in an amount of at least 60% by weight of the total composition;
   a botanical comprising a combination of *Avena sativa* (Oat) Kernel Oil in an amount of from 0.3% to 0.99% by weight of the total composition, Jojoba Esters in an amount of from 3% to 9.99% by weight of the total composition, *Aloe barbadensis* Leaf Extract in an amount of from 0.1% to 0.29% by weight of the total composition and *Bambusa vulgaris* Water in an amount of from 0.01% to 0.09% by weight of the total composition;
   an antioxidant in an amount of least 0.3% by weight of the total composition;
   an exfoliator, the exfoliator comprising *Oryza sativa* Rice Powder in an amount of from 3% to less than 10% by weight of the total composition and *Citrus limon* Peel Powder in an amount of from 3% to less than 10% by weight of the total composition; and
   a lip plumper, the lip plumper comprising Sodium Hyaluronate, *Arnica montana* Flower Extract and Phytonadione.

2. The lip scrub composition of claim 1 wherein the lip plumper comprises Sodium Hyaluronate in an amount of from 0.01% to less than 0.1% by weight of the composition, *Arnica montana* Flower Extract in an amount of from 0.01% to less than 0.1% by weight of the composition and Phytonadione in an amount of from 0.01% to less than 0.1% by weight of the composition.

3. The lip scrub composition of claim 1 wherein the emollient comprises Vegetable Oil, Paraffinum Liquidum, *Helianthus annuus* Seed Oil, *Butyrospermum parkii* Unsaponifiables, Polyglycerin-3, Mango Butter, *Cocos nucifera* (Coconut) Oil, *Theobroma grandiflorum* Seed Butter, *Schinziophyton rautanenii* Seed Oil, *Persea gratissima* Oil, *Orbignya oleifera* Seed Oil, Hydrogenated Moringa Esters, *Punica granatum* Seed Oil, *Oenothera biennis* Oil and *Camellia kissi* Seed Oil.

4. The lip scrub composition of claim 1 wherein the combination of botanicals comprise at least 6% by weight of the total composition.

5. The lip scrub composition of claim 1 wherein the botanical further comprises *Vanilla planifolia* Fruit Extract and *Lavandula angustifolia* Oil.

6. The lip scrub composition of claim 1 further comprising:
   a thickener;
   a vitamin;
   a preservative;
   an emulsifier;
   a humectant; and
   a film former.

7. The lip scrub composition of claim 6 wherein the thickener comprises a combination of Ozokerite Wax, Beeswax, Mango Butter, and *Euphorbia cerifera* Wax.

8. The lip scrub composition of claim 6 wherein the vitamin comprises a combination of Tocopheryl Acetate and Ascorbyl Palmitate.

9. The lip scrub composition of claim 6 wherein the preservative comprises Hydroxyacetophenone.

10. The lip scrub composition of claim 6 wherein the emulsifier comprises a combination of Glyceryl Caprylate and Cetyl Esters.

11. The lip scrub composition of claim 6 wherein the humectant comprises *Crambe abyssinica* Seed Oil.

12. The lip scrub composition of claim 6 wherein the film former comprises a combination of *Acacia decurrens* Flower Wax, *Helianthus annuus* Seed Wax, and *Citrus aurantium dulcis* Peel Wax.

13. A lip scrub composition comprising:
    an emollient in an amount of at least 60% by weight the total composition;
    a thickener in an amount of at least 6% by weight the total composition;
    an exfoliator, the exfoliator comprising *Oryza sativa* Rice Powder in an amount of 3% to less than 10% by weight of the total composition and *Citrus limon* Peel Powder in an amount of from 3% to less than 10% by weight of the total composition;

a botanical in an amount of at least 6% by weight the total composition;
a vitamin in an amount of at least 0.1% by weight the total composition;
an antioxidant in an amount of at least 0.3% by weight the total composition;
a preservative in an amount of at least 0.5% by weight the total composition;
an emulsifier in an amount of at least 0.6% by weight the total composition;
a humectant in an amount of at least 0.02% by weight the total composition; and
a film former in an amount of at least 1% by weight the total composition.

14. The lip scrub composition of claim 13 wherein the botanical comprises *Arnica montana* Flower Extract in an amount of 0.01% to 0.09% by weight of the total composition, the vitamin comprises Phytonadione in an amount of 0.01 to 0.09% by weight of the total composition and the humectant comprises Sodium Hyaluronate in an amount of 0.01% to 0.09%, which in combination increase a volume of a user's lips when applied.

15. The lip scrub composition of claim 13 wherein the botanical comprises at least one botanical selected from the group consisting of *Avena sativa*, (Oat) Kernel Oil, Jojoba Esters, *Aloe barbadensis* Leaf Extract and *Bambusa vulgaris* Water.

16. A composition comprising:
at least 30% by weight Vegetable Oil;
10% to 30% by weight Paraffinum Liquidum;
10% to 30% by weight *Helianthus annuus* Seed Oil;
10% to 30% by weight *Butyrospermum parkii* Unsaponifiables;
3% to 10% by weight Ozokerite Wax;
3% to 10% by weight Beeswax;
3% to 10% by weight *Oryza sativa* Powder;
3% to 10% by weight *Citrus limon* Peel Powder;
3% to 10% by weight Jojoba Esters;
1% to 3% by weight *Acacia decurrens* Flower Wax;
0.3% to 1% by weight *Vanilla planifolia* Fruit Extract;
0.3% to 1% by weight Glyceryl Caprylate;
0.3% to 1% by weight *Helianthus annuus* Seed Wax;
0.3% to 1% by weight Tocopherol;
0.3% to 0.7% by weight Hydroxyacetophenone;
0.3% to 1% by weight Cetyl Esters;
0.3% to 1% by weight *Avena sativa* Kernel Oil;
0.1% to 0.3% by weight Tocopheryl Acetate;
0.1% to 0.3% by weight Polyglycerin-3;
0.1% to 0.3% by weight Mango Butter;
0.1% to 0.3% by weight *Euphorbia cerifera* Wax;
0.1% to 0.3% by weight *Copernicia cerifera* Wax;
0.1% to 0.3% by weight *Cocos nucifera* Oil;
0.1% to 0.3% by weight *Aloe barbadensis* Leaf Extract;
0.01% to 0.1% by weight *Lavandula angustifolia* Oil;
0.01% to 0.1% by weight Ascorbyl Palmitate;
0.01% to 0.1% by weight *Theobroma grandiflorum* Seed Butter;
0.01% to 0.1% by weight *Schinziophyton rautanenii* Seed Oil;
0.01% to 0.1% by weight *Persea gratissima* Oil;
0.01% to 0.1% by weight *Orbignya oleifera* Seed Oil;
0.01% to 0.1% by weight Hydrogenated Moringa Oil Esters;
0.01% to 0.1% by weight *Crambe abyssinica* Seed Oil;
0.01% to 0.1% by weight *Punica granatum* Seed Oil;
0.01% to 0.1% by weight *Oenothera biennis* Oil;
0.01% to 0.1% by weight *Camellia kissi* Seed Oil;
0.01% to 0.1% by weight *Citrus aurantium dulcis* Peel Wax;
0.01% to 0.1% by weight Sodium Hyaluronate;
0.01% to 0.1% by weight *Bambusa vulgaris* Water;
0.01% to 0.1% by weight *Arnica montana* Flower Extract; and
0.01% to 0.1% by weight Phytonadione.

* * * * *